US00PP35292P2

(12) United States Plant Patent
Dirr et al.

(10) Patent No.: US PP35,292 P2
(45) Date of Patent: Aug. 1, 2023

(54) ***LAGERSTROEMIA* PLANT NAMED 'BD-01-20'**

(50) Latin Name: *Lagerstroemia indica*
Varietal Denomination: BD-01-20

(71) Applicant: Premier Introductions, Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 114 days.

(21) Appl. No.: 17/894,373

(22) Filed: Aug. 24, 2022

(51) Int. Cl.
*A01H 5/00* (2018.01)

(52) U.S. Cl.
USPC ..... Plt./252

(58) Field of Classification Search
USPC ..... Plt./252
See application file for complete search history.

*Primary Examiner* — Annette H Para
(74) *Attorney, Agent, or Firm* — Cassandra Bright

(57) ABSTRACT

A new and distinct cultivar of *Lagerstroemia* plant named 'BD-01-20' is disclosed, characterized by compact, upright, intermediate growth habit, reddish new growth, lustrous dark green with red foliage. Flowers are red in color, and highly resistant to *Cercospora* leaf spot. The new variety is a *Lagerstroemia*, normally used for outdoor ornamental purposes.

4 Drawing Sheets

Latin name of the genus and species: *Lagerstroemia indica.*

Variety denomination: 'BD-01-20'.

BACKGROUND OF THE INVENTION

The present invention relates to a new and distinct cultivar of *Lagerstroemia* plant, botanically known as *Lagerstroemia* L, commonly known as crapemyrtle, and hereinafter referred to by the cultivar name 'BD-01-20'. 'BD-01-20' is grown primarily as an ornamental for landscape use.

'BD-01-20' originated from open pollination of *Lagerstroemia* 'GAMAD VI', U.S. Plant Pat. No. 22,161, growing in Watkinsville, Ga., in 2020. The cultivar and was selected from the progeny by continued evaluation for growth habit, foliage, flower, and disease resistance characteristics.

Asexual reproduction of 'BD-01-20' by stem cuttings in Watkinsville, Ga. since 2020 has shown that all the unique features of this new *Lagerstroemia*, as herein described, are stable and reproduced true-to-type through successive generations of such asexual propagation.

SUMMARY OF THE INVENTION

Plants of the new cultivar 'BD-01-20' have not been observed under all possible environmental conditions. The phenotype may vary somewhat with changes in light, temperature, soil and rainfall without, however, any variance in genotype.

The following traits have been repeatedly observed and are determined to be the unique characteristics of 'BD-01-20'. These characteristics in combination distinguish 'BD-01-20' as a new and distinct *Lagerstroemia* cultivar:

1. Compact and tight, dense, intermediate growth habit.
2. Red new growth.
3. Lustrous dark green foliage in summer and maroon in fall.

4. Flowers are reddish shade in color.
5. High resistance to *Cercospora lythracearum* leaf spot.

PARENT COMPARISON

Plants of the new cultivar 'BD-01-20' are similar to plants of the seed parent in most horticultural characteristics; however, plants of the new cultivar 'BD-01-20' differ in the following:

1. 'GAMAD VI' has a Hawaiian punch color new growth, whereas 'BD-01-20' has red new growth.
2. The flowers of 'BD-01-20' are a reddish color, but the flowers of 'GAMAD VI' are red-purple.
3. 'BD-01-20' is smaller, more compact, rounded to broad rounded, however, 'GAMAD VI' has an upright in habit. The pollen parent cannot be identified.

COMMERCIAL COMPARISON

Plants of the new cultivar 'BD-01-20' are comparable to the commercial variety *Lagerstroemia* 'GAMAD I', unpatented. The two *Lagerstroemia* varieties are similar in most horticultural characteristics, however, the new variety 'BD-01-20' differs in the following;

1. 'BD-01-20 has red new foliage growth and lustrous dark green and red foliage, however 'GAMAD I' has bronze new leaves that mature to dark green.
2. 'GAMAD-I' has smaller leaves, about half the size of 'BD-01-20'.

Plants of the new cultivar 'BD-01-20' are comparable to the commercial variety *Lagerstroemia* 'PIILAG-VII', U.S. Plant Pat. No. 27,303. The two *Lagerstroemia* varieties are similar in most horticultural characteristics; however, the new variety 'BD-01-20' differs in the following;

1. Flowers of 'BD-01-20' are reddish in color and the stamens (are exposed/visible), whereas 'PIILAG-VII' has flowers that are red in color and the stamens are covered by the petals.

2. 'PIILAG-VII' has shiny green foliage and is a taller plant with a looser habit, but 'BD-01-20' has green-purple foliage and a tighter more compact habit.

BRIEF DESCRIPTION OF THE PHOTOGRAPHS

The accompanying photograph in FIG. 1 illustrates a close-up view of the flower of 'BD-01-20'.

Figure 1:
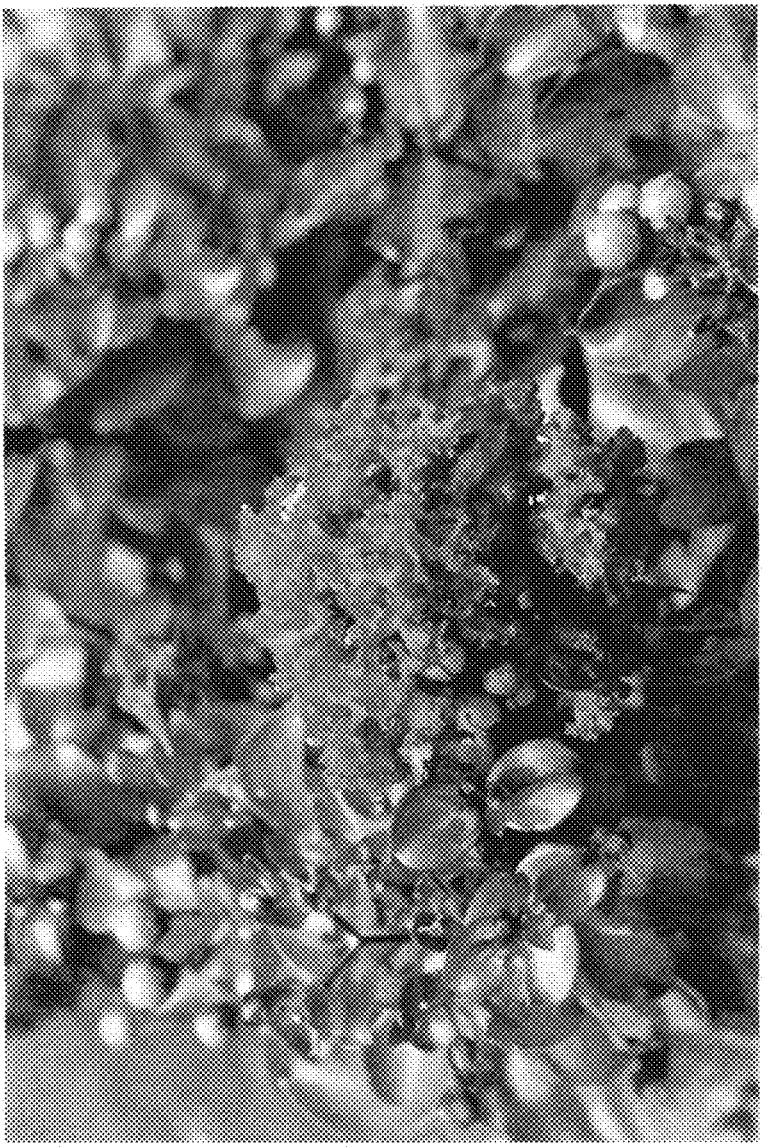
Figure 2:
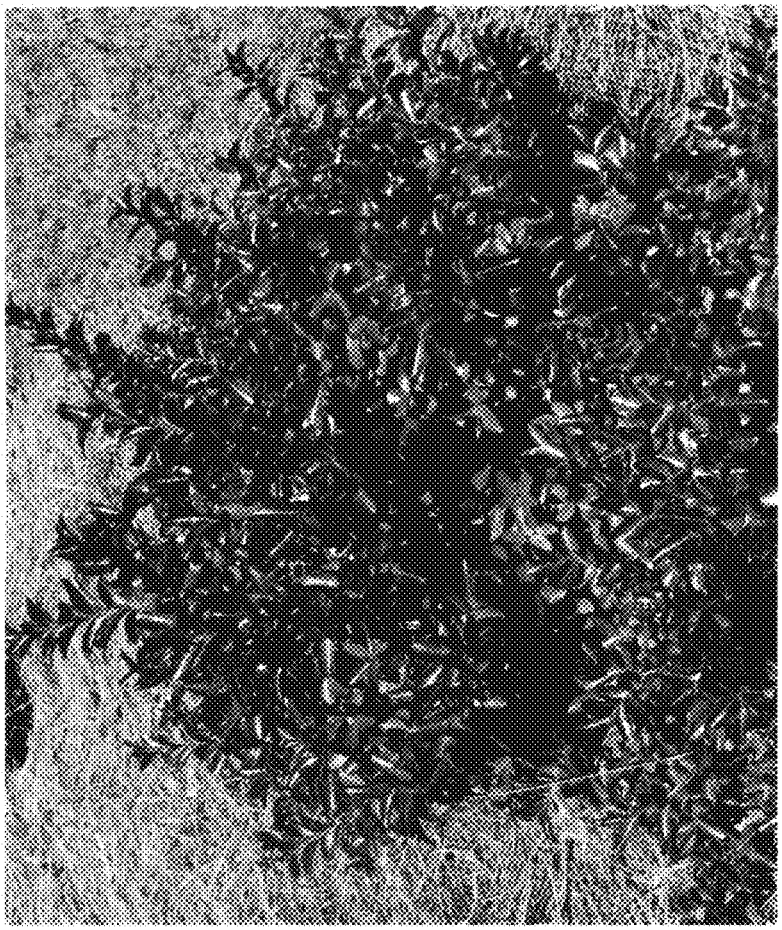
FIG. 2 illustrates a view of 'BD-01-20' in the ground.
Figure 3:
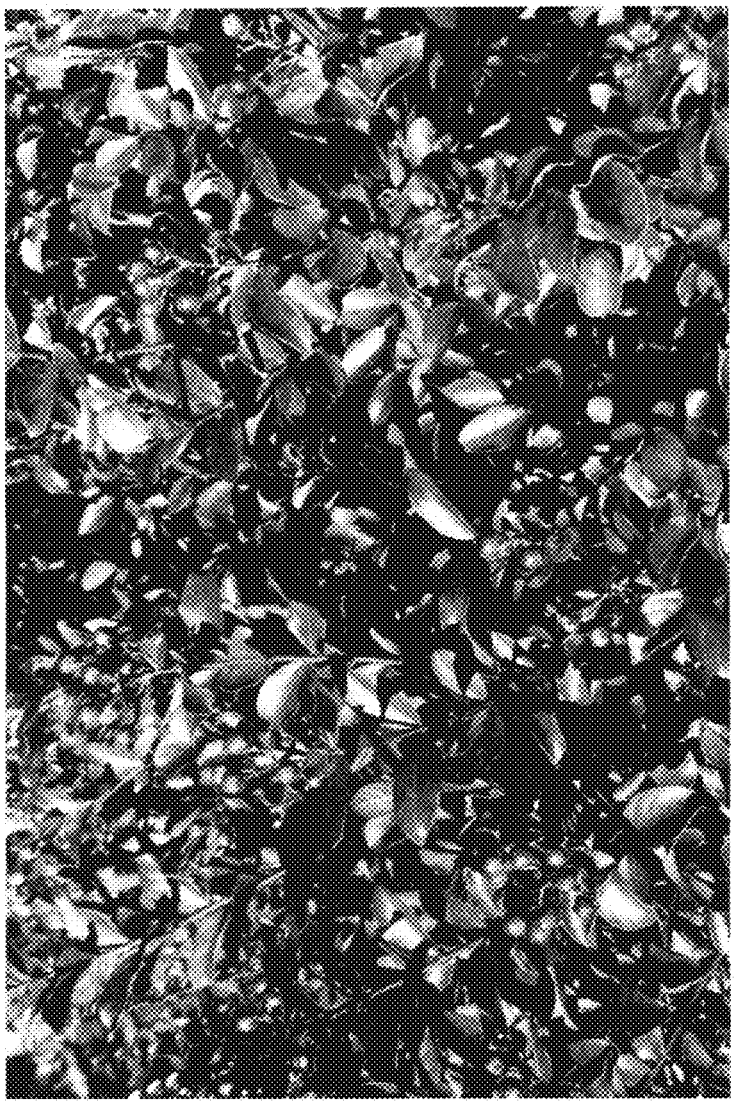
FIG. 3 illustrates the fall color of 'BD-01-20'.
Figure 4:
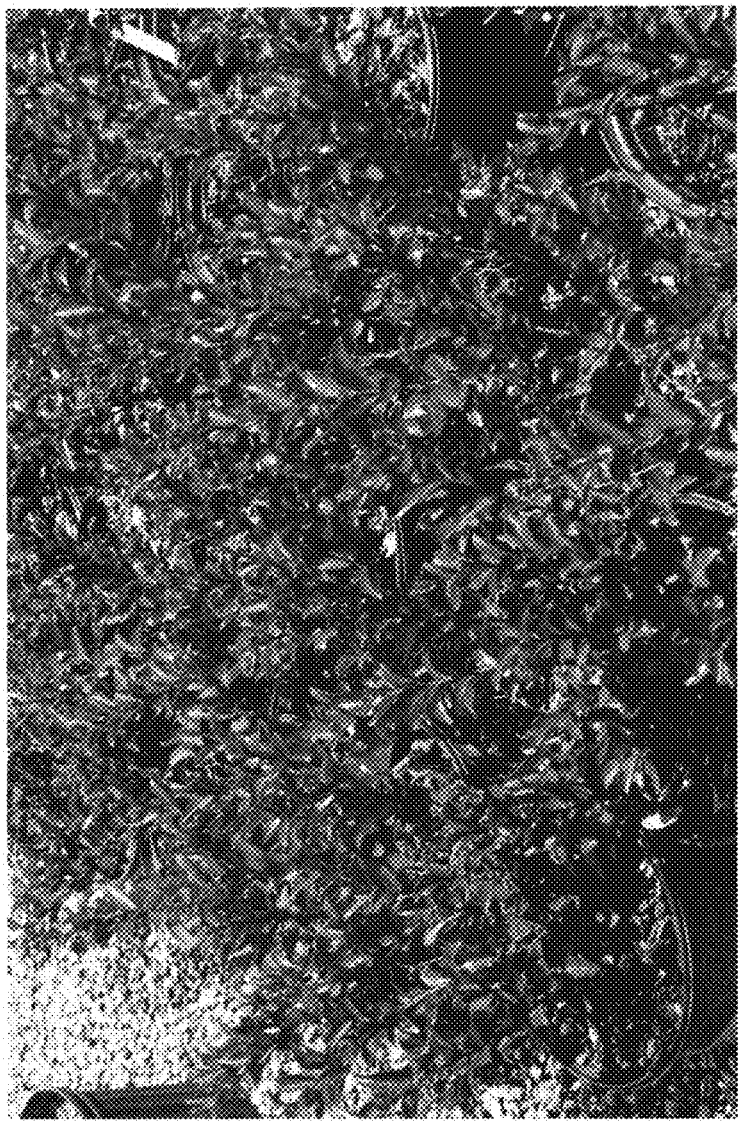
FIG. 4 illustrates the color of the new growth. Plants photographed are approximately 1.5 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2015 Edition, except where general terms of ordinary dictionary significance are used. Plants used for the description were approximately two-years-old and were grown in 23.03 L containers under outdoor conditions in Watkinsville, Ga. Colors are described using The Royal Horticultural Society Colour Chart (R.H.S.).

Botanical classification: *Lagerstroemia indica* 'BD-01-20'.

PROPAGATION

Type of propagation typically used: Terminal stem cuttings.

Time to initiate roots: About 21 days at about 32° C.

Time to produce a rooted cutting: Average 3 months at about 32° C.

Root description: Numerous, fine, fibrous and well-branched. Color: RHS White NN155C.

PLANT

Age of plant described: About 2 years.

Container size: 23.03-liter container.

Plant form: Upright, compact flowering shrub.

Growth habit: Compact, tight, dense.

Plant spread: 96 cm.

Plant height: 71 cm.

Branching habit: Freely branching; lateral branches abundant without pruning.

First year stems:
- *Length.*—30 to 40 cm.
- *Diameter.*—2.5 mm.
- *Color.*—New growth: RHS Red 59A. Woody: RHS Brown 200D.
- *Shape.*—Squarish.
- *Strength.*—Flexible.

Second year stems:
- *Length.*—60 to 90 cm.
- *Color.*—RHS Brown N199B.
- *Shape.*—Terete.
- *Strength.*—Flexible.

Trunk:
- *Diameter.*—3 cm at soil line.
- *Color.*—RHS Brown 199A.

Internode length: About 1.5 cm.

Vegetative buds:
- *Arrangement.*—Sub-opposite to alternate, imbricate, conical.
- *Pubescence.*—None.
- *Length.*—2.5 cm.
- *Width.*—1 mm.
- *Color.*—RHS Red 59A.

FOLIAGE

Leaf:
- *Arrangement.*—Sub-opposite to alternate, simple.
- *Average length.*—4 cm.
- *Average width.*—2 cm.
- *Shape of blade.*—Elliptical to ovate, with undulating surface.
- *Apex.*—Acuminate.
- *Base.*—Cuneate.
- *Margin.*—Entire.
- *Texture of top surface.*—Glabrous and glossy.
- *Texture of bottom surface.*—Glabrous and glossy.
- *Color.*—Young foliage upper side: RHS Red 59A. Young foliage under side: RHS Red 59A. Mature foliage upper side: RHS Green N137A. Mature foliage under side: RHS Green 137C. Fall color: Can be RHS Red 59A, 59C, and Reddish Purple N77A, or any combination of these colors. Venation: Type: Pinnate. Immature Venation color, upper side: RHS Red 59B. Immature Venation color, under side: RHS Yellow-Green N144A. Mature Venation color, upper side: RHS Yellow-Green 145A. Mature Venation color, under side: RHS Yellow-Green 145C.
- *Petiole.*—Length: 2 mm. Diameter: 1 mm. Color, upper and lower surfaces: RHS Red 59A. Pubescence: None.

FLOWER

Natural flowering season: June to September. An inflorescence is showy for about two weeks, individual flowers last about one day.

Inflorescence form: Panicle.

Flowers per inflorescence: 30 to 35 flowers and buds.

Inflorescence size:
- *Width.*—10 cm.
- *Height.*—12 cm.

Individual flowers:
- *Diameter.*—3 cm.
- *Height.*—2 cm.
- *Persistence.*—Self-cleaning.
- *Fragrance.*—Lightly fragrant.

Petals:
- *Number.*—6 to 7.
- *Shape.*—Fan-shaped.
- *Margin.*—Undulate.
- *Tip.*—Ruffled, rounded.
- *Base.*—Sagittate.
- *Length.*—1.5 cm.
- *Width.*—1.3 cm.
- *Texture.*—Upper: Glabrous. Lower: Glabrous.
- *Color.*—Upper surface: RHS Red 53C. Under surface: RHS Red 53C.

Bud:
- *Shape.*—Globose with six distinct lines of dehiscence where they split to reveal the petals.
- *Length.*—1 cm.

*Diameter.*—1 cm.
*Color.*—RHS Red 59A.

Calyx:
*Shape.*—Unguiculate.
*Length.*—8 mm.
*Diameter.*—1 cm.

Sepals:
*Arrangement.*—Single whorl of 6 basally fused sepals, separated at the apex.
*Shape.*—Elliptical.
*Apex.*—Acute.
*Margin.*—Entire.
*Length.*—9 mm.
*Width.*—4 mm.
*Margin.*—Entire.
*Texture.*—Upper: Smooth, glabrous. Lower: Smooth, glabrous.
*Color.*—When opening, upper: RHS Red 179A. When opening, lower: RHS Red 179B.

Pedicel:
*Length.*—8 mm.
*Diameter.*—1 mm.
*Pubescence.*—None.
*Color.*—RHS Red 179B.

Calyx:
*Length.*—8 mm.
*Diameter.*—1 cm.
*Pubescence.*—None.
*Color.*—RHS Red 179B.

REPRODUCTIVE ORGANS

Stamens:
*Quantity/arrangement.*—About 25 to 30 short stamens clustered in the center, about 1.5 cm in length; surrounded by 6 longer stamens, about 2 cm in length.
*Filament color.*—RHS Yellowish Pink 35C.

Anthers:
*Color.*—RHS Yellow 7A.
*Pollen.*—Moderate, RHS Yellow 7A in color.

Pistil:
*Number.*—1 superior pistil per flower.
*Length.*—1.9 cm.

Stigma:
*Shape.*—Round.
*Diameter.*—1 mm.
*Color.*—RHS Reddish Orange N172A.
*Ovary color.*—RHS Yellow 2B.
*Ovary diameter.*—2.5 mm.

OTHER CHARACTERISTICS

Fruit:
*Type/appearance.*—6-valved, dehiscent, broad ellipsoidal capsule.
*Length.*—8 mm.
*Diameter.*—8 mm.
*Color, immature.*—RHS Yellow-Green 144B.
*Color, mature.*—RHS Brown 200C.

Seeds:
*Quantity.*—30 per capsule.
*Length.*—5 mm.
*Diameter.*—3 mm.
*Color.*—RHS Brown 200C.

Disease/pest resistance: Plants of the claimed *Lagerstroemia* variety grown in container trials have exhibited high resistance to *Cercospora lythracearum* leaf spot.

Temperature range: USDA Hardiness Zone Map (2012): Zone 6 to 9.

What is claimed is:

1. A new and distinct cultivar of *Lagerstroemia* plant named 'BD-01-20' as herein illustrated and described.

* * * * *